US 6,699,245 B2

(12) United States Patent
Dinger et al.

(10) Patent No.: US 6,699,245 B2
(45) Date of Patent: Mar. 2, 2004

(54) ANASTOMOSIS SYSTEM AND RELATED METHODS

(75) Inventors: Fred Dinger, Sacramento, CA (US); Paul Charbonneau, Sacramento, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 10/068,777

(22) Filed: Feb. 5, 2002

(65) Prior Publication Data

US 2002/0128672 A1 Sep. 12, 2002

Related U.S. Application Data (60) Provisional application No. 60/266,694, filed on Feb. 5, 2001.

(51) Int. Cl.[7] .............................................. A61B 18/08
(52) U.S. Cl. ............................ 606/49; 606/45; 606/41
(58) Field of Search ............................ 606/41, 45, 48, 606/49

(56) References Cited

U.S. PATENT DOCUMENTS

| | | |
|---|---|---|
| 4,350,160 A | 9/1982 | Kolesov et al. |
| 4,366,819 A | 1/1983 | Kaster |
| 4,368,736 A | 1/1983 | Kaster |
| 4,624,257 A | 11/1986 | Berggren et al. |
| 4,662,068 A | 5/1987 | Polonsky |
| 4,892,098 A | 1/1990 | Sauer |
| 4,917,090 A | 4/1990 | Berggren et al. |
| 4,917,091 A | 4/1990 | Berggren et al. |
| 4,955,378 A | 9/1990 | Grasso |
| 5,071,417 A | 12/1991 | Sinofsky |
| 5,140,984 A | 8/1992 | Dew et al. |
| 5,156,613 A | 10/1992 | Sawyer |
| 5,217,458 A * | 6/1993 | Parins .......................... 606/48 |
| 5,234,447 A | 8/1993 | Kaster et al. |
| 5,249,192 A | 9/1993 | Kuizenga et al. |
| 5,272,716 A | 12/1993 | Soltz et al. |
| 5,290,278 A | 3/1994 | Anderson |
| 5,300,065 A | 4/1994 | Anderson |
| 5,334,191 A | 8/1994 | Poppas et al. |
| 5,336,221 A | 8/1994 | Anderson |
| 5,354,323 A | 10/1994 | Whitebook |
| 5,364,389 A | 11/1994 | Anderson |
| 5,403,312 A | 4/1995 | Yates et al. |
| 5,409,479 A | 4/1995 | Dew et al. |
| 5,409,781 A | 4/1995 | Rösler et al. |
| 5,531,744 A | 7/1996 | Nardella et al. |
| 5,540,684 A | 7/1996 | Hassler, Jr. |
| 5,571,216 A | 11/1996 | Anderson |
| 5,612,050 A | 3/1997 | Rowe et al. |
| 5,624,452 A | 4/1997 | Yates |
| 5,662,643 A | 9/1997 | Kung et al. |
| 5,665,085 A | 9/1997 | Nardella |
| 5,693,051 A | 12/1997 | Schulze et al. |
| 5,709,680 A | 1/1998 | Yates et al. |

(List continued on next page.)

OTHER PUBLICATIONS

Carter, Lt. E..L. et al; "Direct Nonsuture Coronary Artery Anastomosis in the Dog" Annals of Surgery, Vol 148, Issue 2, 1958 pp. 212–218.

Goetz, R.H., M.D. et al., "Internal mammary–Coronary Artery Anastomosis–A Nonsuture Method Employing Tantalum Rings", Journal of Thoracic and Cardiovascular Surgery, Vol 41, Issue 3, 1961, pp. 378–836.

*Primary Examiner*—Lee Cohen
*Assistant Examiner*—Aaron Roane
(74) *Attorney, Agent, or Firm*—Ryan Kromholz & Manion, S.C.

(57) ABSTRACT

Devices and methods for sealingly joining a graft vessel, such as a coronary bypass graft, to the side wall of a target vessel, such as the aorta or a coronary artery, in an anastomosis.

2 Claims, 11 Drawing Sheets

U.S. PATENT DOCUMENTS

| | | | |
|---|---|---|---|
| 5,725,522 A | | 3/1998 | Sinofsky |
| 5,749,895 A | * | 5/1998 | Sawyer et al. ............... 606/214 |
| 5,810,811 A | | 9/1998 | Yates et al. |
| 5,824,015 A | | 10/1998 | Sawyer |
| 5,827,265 A | | 10/1998 | Glinsky et al. |
| 5,833,690 A | | 11/1998 | Yates et al. |
| 5,846,241 A | * | 12/1998 | Kittur et al. ................... 606/48 |
| 5,865,830 A | | 2/1999 | Parel et al. |
| 5,871,524 A | | 2/1999 | Knowlton |
| 5,876,401 A | | 3/1999 | Schulze et al. |
| 5,925,078 A | | 7/1999 | Anderson |
| 6,004,335 A | | 12/1999 | Vaitekunas et al. |
| 6,033,401 A | | 3/2000 | Edwards et al. |
| 6,083,223 A | | 7/2000 | Baker |
| 6,086,586 A | | 7/2000 | Hooven |
| 6,087,552 A | | 7/2000 | Gregory |
| 6,110,188 A | | 8/2000 | Narciso, Jr. |
| 6,113,598 A | | 9/2000 | Baker |
| 6,113,612 A | | 9/2000 | Swanson et al. |
| 6,126,658 A | | 10/2000 | Baker |
| 6,132,429 A | | 10/2000 | Baker |
| 6,171,319 B1 | | 1/2001 | Nobles et al. |
| 6,176,854 B1 | | 1/2001 | Cone |

\* cited by examiner

ANASTOMOSIS SYSTEM AND RELATED METHODS

RELATED APPLICATION

This application claims the benefit of U.S. Provisional Application Ser. No. 60/266,694 filed Feb. 5, 2001.

FIELD OF THE INVENTION

The present invention relates generally to medical devices and methods for welding biological tissue. In particular, the invention relates to performing a vascular anastomosis and, more particularly, to preferred devices and methods for sealingly joining a graft vessel, such as a coronary bypass graft, to the side wall of a target vessel, such as the aorta or a coronary artery, in an anastomosis.

BACKGROUND OF THE INVENTION

A wide variety of medical procedures involve creating an anastomosis to establish fluid communication between two tubular conduits or organs in a patient. Coronary artery bypass graft (CABG) surgery, for example, often involves creating an anastomosis between blood vessels or between a blood vessel and a vascular graft to create or restore a blood flow path to the heart muscles. Such CABG surgery is necessary to overcome coronary artery disease, wherein plaque build-up on the inner walls of the coronary arteries causes narrowing or complete closure of these arteries. This results in insufficient blood flow and deprives the heart muscle of oxygen and nutrients, leading to ischemia, possible myocardial infarction, and even death. CABG surgery may be performed via a traditional open-chest procedure or a closed-chest or port-access thoracoscopic procedure.

CABG surgery may require the creation of one or more anastomosis depending upon whether a "free graft" or a "pedicle graft" is employed. A "free graft" is a length of conduit having open proximal and distal ends. A proximal anastomosis is required to connect the proximal end of the graft to a source of blood (e.g. the aorta) and a distal anastomosis is required to connect the distal end of the graft to the target vessel (e.g. a coronary artery). Free grafts may be autologous, such as by harvesting a saphenous vein or other venous or arterial conduit from elsewhere in the body, or an artificial conduit, such as Dacron or Goretex tubing. A "pedicle graft" is the result of rerouting a less essential artery, such as the internal mammary artery, from it native location so that it may be connected to the coronary artery downstream of the blockage. The proximal end of the graft vessel remains attached in its native position and only one anastomosis is required to connect the distal end of the graft vessel to the target vessel. In either case, the anastomosis may be between the end of the graft and an aperture in the side wall of the source or target vessel (a so-called "end-to-side" anastomosis) or the anastomosis may be between an aperture in the side wall of the graft and an aperture in the side wall of the source or target vessel (a so-called "side-to-side" anastomosis).

Current methods available for creating an anastomosis include hand suturing the vessels together. Connection of interrupted vessels with stitches has inherent drawbacks. For example, it is difficult to perform and requires great skill and experience on the part of the surgeon due in large part to the extremely small scale of the vessels. Coronary arteries typically have a diameter in the range of between about 1 to 5 mm, and the graft vessels have a diameter on the order of about 1 to 4 mm for an arterial graft such as a mammary artery, or about 4 to 8 mm for a vein graft such as a saphenous vein. In closed-chest or port access procedures, the task of suturing is even more challenging due to the use of elongated instruments positioned through the access ports for approximating the tissues and for holding and manipulating the needles and sutures used to make the anastomoses. Other drawbacks of connection with stitches are the long duration of the operation, during which period in conventional open-heart CABG surgery the heart is arrested and the patient is maintained under cardioplegic arrest and cardiopulmonary bypass. Cardiopulmonary bypass has been shown to be the cause of many of the complications that have been reported in conventional CABG, such as stroke. The period of cardiopulmonary bypass should be minimized, if not avoided altogether, to reduce patient morbidity.

One approach to coronary artery bypass grafting that avoids cardiopulmonary bypass is performing the suturing procedure on a beating heart. At present, however, safe, reproducible, and precise anastomosis between a stenotic coronary artery and a bypass graft vessel presents numerous obstacles including continuous cardiac translational motion which makes meticulous microsurgical placement of graft sutures extremely difficult. The constant translational motion of the heart and bleeding from the opening in the coronary artery hinder precise suture placement in the often tiny coronary vessel.

The above mentioned drawbacks of hand suturing have led to the development of various approaches to stichless vascular anastomosis. One approach involves the use of rigid rings, such a described in Geotz et al., INTERANL MAMMARY-CORONARY ARTERY ANASTOMOSIS-A Nonsuture Method Employing Tantalum Rings, J. Thoracic and Cardiovasc. Surg. Vol. 41 No. 3, 1961, pp. 378–386. This anastomosis method uses polished siliconized tantalum rings that are circumferentially grooved. The free end of the internal mammary is passed through a ring chosen according to the size of the stenotic coronary artery. The free end of the mammary artery is everted over one end of the ring as a cuff and fixed with a silk ligature that is tied around the most proximal of the circular grooves in the ring. The cuffed internal mammary artery is inserted into an incision in the target coronary artery. The ring is fixed in place and sealingly joined to the target coronary artery by tying one or more sutures circumferentially around the target vessel and into one or more circular grooves in the ring. An intimal-to-intimal anastomosis results and dissection of blood between the coronary artery and the cuffed internal mammary artery is largely prevented.

Other ring-related anastomotic approaches include that disclosed in Carter et al., Direct Nonsuture Coronary Artery Anastomosis in the Dog, Annals of Surgery, Volume 148, No. 2, 1958, pp. 212–218, and U.S. Pat. No. 4,624,257 to Berggren et al. However, no permanently satisfactory results have been reported with the use of rigid rings. A rigid ring presents a foreign body of relatively heavy weight which does not heal well and produces pressure necrosis. Moreover, the use of rigid rings that completely encircle the graft vessel and the arteriotomy creates a severe "compliance mismatch" relative to both the coronary artery and the graft vessel and the anastomosis site which could lead to thrombosis. That is, recent studies suggest that the anastomosis site should not be dramatically different in compliance relative to either the coronary artery or the vascular graft, which is the case when using rigid rings to sealingly join two vessels together.

Other attempts at stitchless anastomosis involve the use of stapling devices. For example, U.S. Pat. No. 4,350,160 discloses a vascular stapling device for creating an end-to-end anastomosis between the internal mammary artery (IMA) or a vein graft and one of the coronary arteries, primarily the left anterior descending coronary artery (LAD). However, this device can only perform end-to-end anastomoses such that the coronary artery must first be severed and dissected from the surrounding myocardium and the exposed end everted for attachment. This technique is limited to cases where the coronary artery is totally occluded and there is no loss of blood flow by completely severing the coronary artery downstream of the blockage to make the anastomosis. Consequently, this device is not applicable where the coronary artery is only partially occluded and is not at all applicable to making the proximal side-to-end anastomosis between a bypass graft and the aorta.

U.S. Pat. No. 5,234,447 discloses a vascular stapling device for end-to-side vascular anastomoses. A ring-shaped staple is provided having legs extending from the proximal and distal ends of the ring for joining two blood vessels together in an end-to-side anastomosis. However, this device does not provide a complete system for quickly and automatically performing an anastomosis. Rather, it involves a great deal of manual manipulation of the staple, using hand operated tools to individually deform the distal lines of the staple after the graft has been attached and before it is inserted into the opening made in the aortic wall. One of the more difficult maneuvers in applying the staple involves carefully everting the graft vessel over the sharpened ends of the staple legs, then piercing the everted edge of the vessel with the staple legs. Experimental attempts to apply this technique have proven to be very problematic because of difficulty in manipulating the graft vessel and the potential for damage to the graft vessel wall. For speed, reliability and convenience, it is preferable to avoid the need for complex maneuvers while performing the anastomosis. Further bending operations must then be performed on the staple legs. Once the distal lines of the staple have been deformed, it may be difficult to insert the staple through the aortotomy opening.

Another disadvantage of the device of the '447 patent is that the distal lines of the staple pierce the wall of the graft vessel at the point where it is everted over the staples. Piercing the wall of the graft vessel potentially invites leaking of the anastomosis and may compromise the structural integrity of the graft vessel wall, serving as a locus for a dissection or even a tear which could lead to catastrophic failure. Because the staple legs only apply pressure to the anastomosis at selected points, there is a potential for thrombosis. There is also the potential that exposure of the medial layers of the graft vessel where the staple pierces the wall could be a site for the onset of intimal hyperplasia, which would compromise the long-term patency of the graft. Because of these potential drawbacks, it is desirable to make the attachment to the graft vessel as atraumatic to the vessel wall as possible and to eliminate as much as possible the exposure of any foreign materials or any vessel layers other than a smooth uninterrupted intimal layer within the anastomosis site or within the graft vessel lumen.

Still other anastomotic approaches involve the use of anastomotic fittings for joining blood vessels together. U.S. Pat. No. 4,366,819, for example, discloses a vascular anastomotic fitting device for end-to-side vascular anastomoses. This device is a four-part anastomotic fitting having a tubular member over which the graft vessel is everted, a ring flange which engages the aortic wall from within the aortic lumen, and a fixation ring and a locking ring which engage the exterior of the aortic wall. Another similar device is described in U.S. Pat. No. 4,368,736. This device is a tubular fitting with a flanged distal end that fastens to the aortic wall with an attachment ring, and a proximal end with a graft fixation collar for attaching to the graft vessel. These devices have a number of drawbacks that the present invention seeks to overcome. Firstly, the anastomotic fittings described expose the foreign material of the anastomotic device to the blood flow path within the arteries. This is undesirable because foreign materials within the blood flow path can have a tendency to cause hemolysis, platelet deposition and thrombosis. Immune responses to foreign material, such as rejection of the foreign material or auto-immune responses triggered by the presence of foreign material, tend to be stronger when the material is exposed to the bloodstream. As such, it is preferable that as much as possible of the interior surfaces of an anastomotic fitting that will be exposed to the blood flow path be covered with vascular tissue, either from the target vessel or from the graft vessel, so that a smooth, continuous, hemocompatible endothelial layer will be presented to the bloodstream. The anastomotic fitting of the '819 patent also has the potential drawback that the spikes that hold the graft vessel onto the anastomotic fitting are very close to the blood flow path, potentially causing trauma to the blood vessel that could lead to leaks in the anastomosis or compromise of the mechanical integrity of the vessels. Consequently, it is desirable to provide an anastomosis fitting that is atraumatic to the graft vessel as possible. Any sharp features such as attachment spikes should be placed as far away from the blood flow path and the anastomosis site as possible so that there is no compromise of the anastomosis seal or the structural integrity of the vessels.

Another device, the 3M-Unilink device for end-to-end anastomosis (U.S. Pat. Nos. 4,624,257; 4,917,090; 4,917,091) is designed for use in microsurgery, such as for reattaching vessels severed in accidents. This device provides an anastomosis clamp that has two eversion rings which are locked together by a series of impaling spikes on their opposing faces. However, this device is awkward for use in end-to-side anastomosis and tends to deform the target vessel; therefore it is not currently used in CABG surgery. Due to the delicate process needed to insert the vessels into the device, it would also be unsuitable for port-access surgery.

In order to solve these and other problems, it is desirable to provide an anastomosis device capable of performing end-to-side and/or side-to-side anastomosis between blood vessels or other hollow organs and vessels. It is also desirable to provide an anastomosis device which minimizes the amount of foreign materials exposed to the blood flow path within the blood vessels and which avoids leakage problems, and which promotes rapid endothelialization and healing. Further, it would be desirable to provide such a device which could be used in port-access CABG surgery. Whether it is used with open-chest or closed-chest surgical techniques, it is also desirable that the invention provide a complete system for quickly and automatically performing an anastomosis with a minimal amount of manual manipulation.

SUMMARY OF THE INVENTION

The present invention involves an anastomosis system and method suitable, by way of example, for use in establishing fluid communication between a graft conduit and a blood vessel in coronary artery bypass graft (CABG) surgery. The anastomosis system of the present invention establishes such fluid communication by employing tissue fusion technology to effectively fuses the graft conduit to the blood vessel, thereby eliminating the need for connectors or similar prior art devices that remain implanted following the anastomosis procedure. The system may be used to create side-to-side and/or end-to-side anastomosis connections. It may also be employed in either open-chest or closed chest procedures.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be routine undertaking for those of ordinary skill in the art having the benefit of this disclosure. It is furthermore to be readily understood that, although discussed below primarily within the context of coronary artery bypass graft surgery (CABG), the anastomosis system of the present invention may be employed in any number of applications and/or procedures wherein it is desired to establish fluid communication between two conduits. The anastomosis system and method disclosed herein boasts a variety of inventive features and attributes that warrant patent protection, both individually and in combination.

Figure 1:
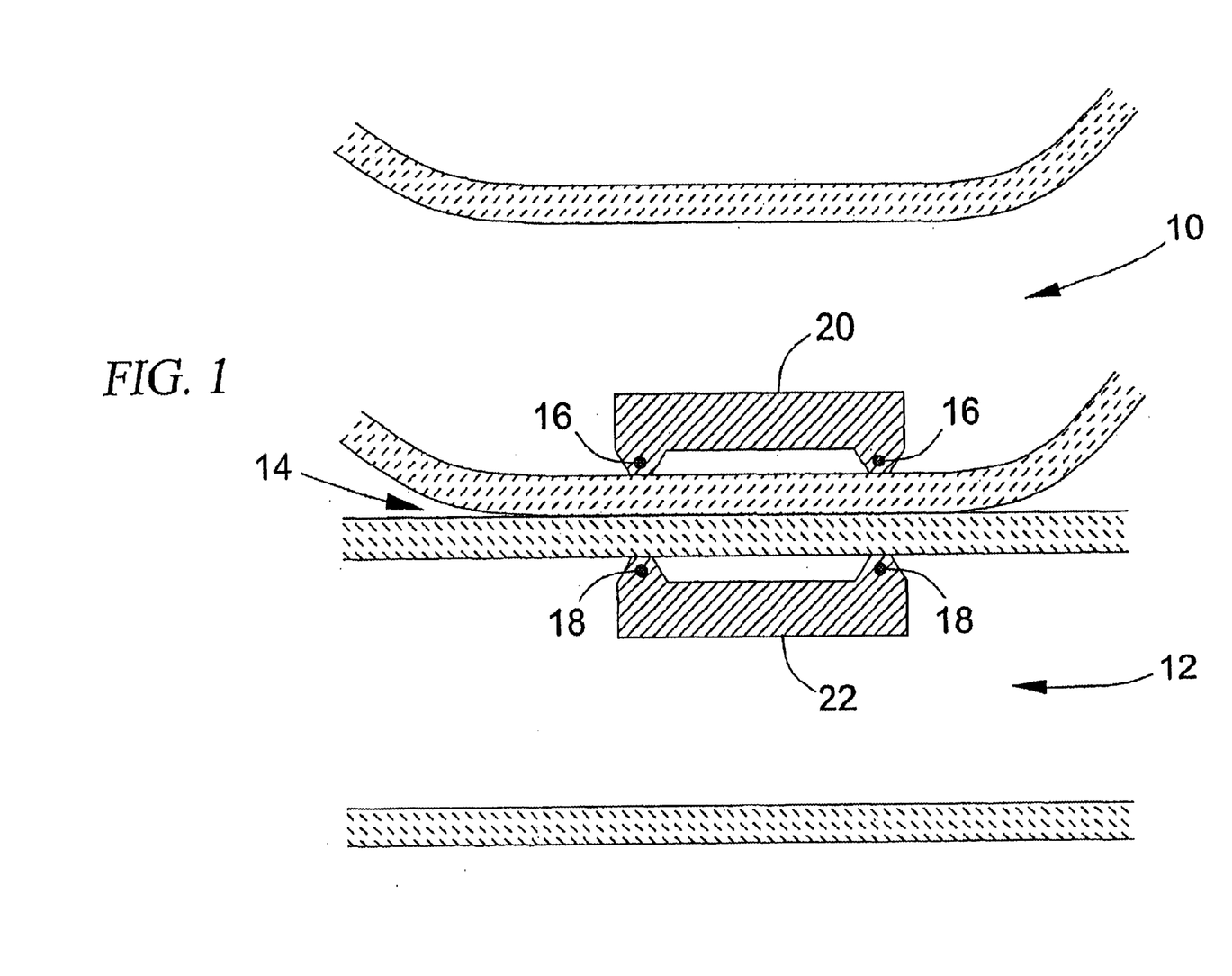
FIG. 1 is a cross-sectional view illustrating an anastomosis method according to a broad principle of the present invention for creating a side-to-side anastomosis between a graft conduit and a blood vessel.
Figure 2:
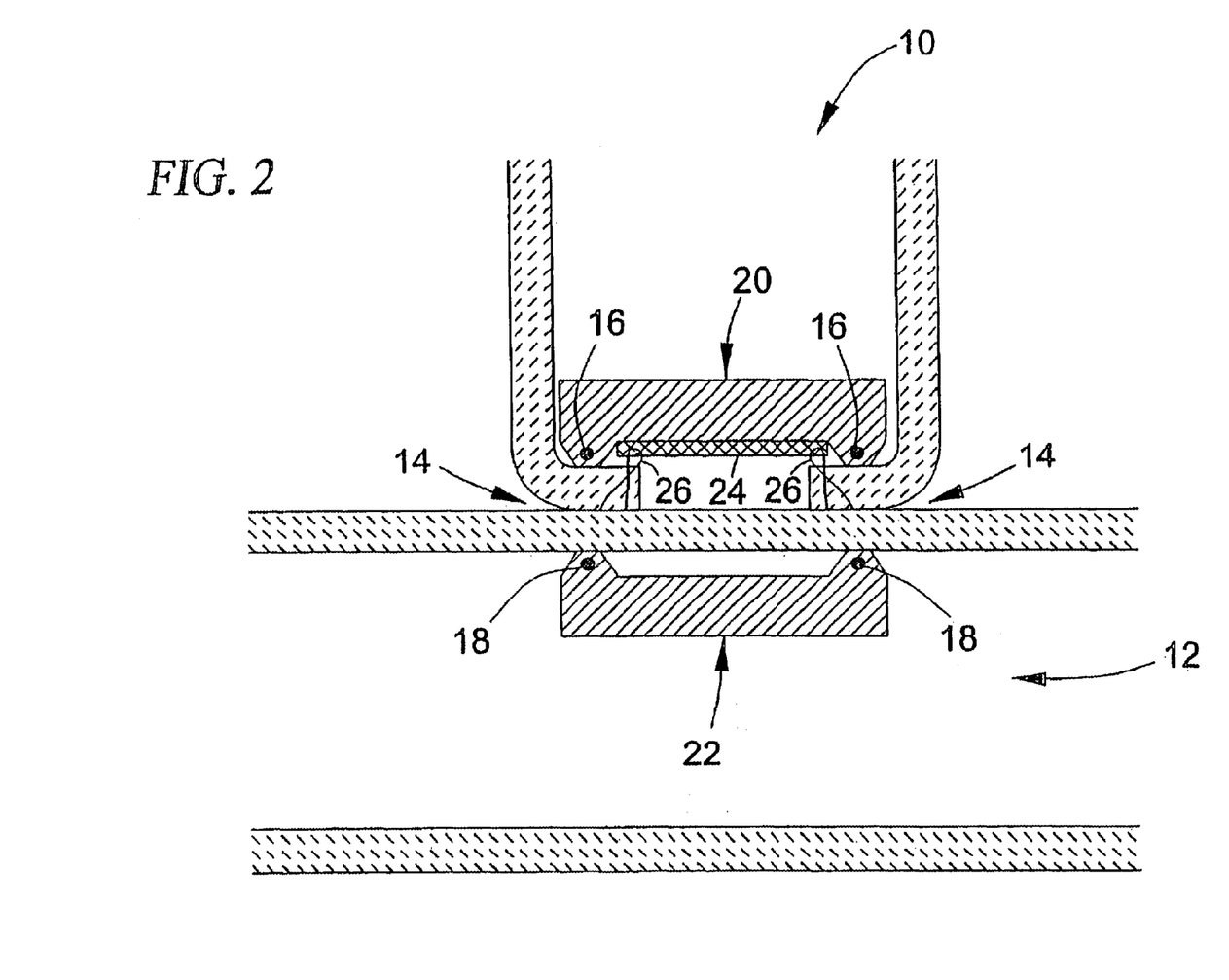
FIG. 2 is a cross-sectional view illustrating an anastomosis method according to a broad principle of the present invention for creating an end-to-side anastomosis between a graft conduit and a blood vessel.

A broad aspect of the anastomosis system and method of the present invention involves fusing a graft conduit to a blood vessel. The present invention advantageously provides the ability to create either a "side-to-side" anastomosis (FIG. 1) or an "end-to-side" anastomosis (FIG. 2). In either event, the anastomosis is created according to the present invention by: (a) positioning a length of graft conduit 10 in generally mating relationship with a length of blood vessel 12 to establish a graft mating region 14; (b) disposing first and second generally ring-shaped tissue fusion element 16, 18 on either side of the graft mating region 14; and (c) activating at least one of the tissue fusion element 16, 18 to fuse the graft conduit 10 to the blood vessel 12. The graft conduit 10 may be a "free graft" or a "pedicle graft." A "free graft" will require a proximal anastomosis to connect the proximal end of the graft to a source of blood (e.g. the aorta) and a distal anastomosis to connect the distal end of the graft to the target vessel (e.g. a coronary artery). Free grafts may be autologous, such as by harvesting a saphenous vein or other venous or arterial conduit from elsewhere in the body, or an artificial conduit, such as Dacron or Goretex tubing. A "pedicle graft" will require only one anastomosis to connect the distal end of the graft vessel (e.g. internal mammary artery) to the target vessel.

The first and second tissue fusion elements 16, 18 may comprise any number of electrodes, devices, or components capable of establishing a suitable union between the graft conduit 10 and the blood vessel 12. These tissue fusion or tissue welding technologies may include, but are not necessarily limited to, so-called "wet electrode" technology; radio-frequency (RF) technology; ultrasonic technology; bi-polar technology, mono-polar technology, a-polar technology, laser technology, or any other technology (including but not limited to pressure and/or heat) capable of welding or fusing the graft conduit 10 to the blood vessel 12. Generally speaking, the application of such technology enables causes the extracellular proteins (e.g. collagen) within the graft and/or blood vessel wall to become denatured and act as a biological glue and/or to become cross-linked. In this fashion, the opposed surfaces of the graft conduit 10 and blood vessel 12 are welded or fused together to produce a leak-free junction. Such tissue fusion or tissue welding technologies may be disclosed in one or more of U.S. Pat. Nos. 4,892,098, 4,955,378, 5,071,417, 5,140,984, 5,156,613, 5,249,192, 5,272,716, 5,290,278, 5,300,065, 5,334,191, 5,336,221, 5,354,323, 5,364,389, 5,403,312, 5,409,479, 5,409,781, 5,531,744, 5,540,684, 5,571,216, 5,612,050, 5,624,452, 5,662,643, 5,665,085, 5,693,051, 5,709,680, 5,725,522, 5,749,895, 5,810,811, 5,824,015, 5,833,690, 5,865,830, 5.871,524, 5,876,401, 5,925,078, 6,004,335, 6,033,401, 6,083,223, 6,086,586, 6,087,552, 6,113,598, 6,126,658, 6,132,429, and 6,176,854, the disclosures of which are hereby expressly incorporated into this specification as if set forth fully herein.

In a preferred embodiment, the first and second tissue fusion elements 16, 18 are each dimensioned to encompass a generally circular area on the graft conduit 10 and blood vessel 12. That is, the first and second tissue fusion elements 16, 18 are generally ring-shaped such that, when disposed on opposed sides of the graft mating region 14, a generally circular region is defined within the mating region 14. Upon activation for an effective period, the first and second tissue fusion elements 16, 18 weld or fuse the graft conduit 10 and the blood vessel 12 about the periphery of the generally circular region with the mating region 14. In a preferred embodiment, the first and second tissue fusion elements 16, 18 are designed to cut or sever through the tissue at the same general time the fusion or welding is taking place. In this fashion, a generally circular union is formed in the approximate area of the ring-shaped first and second tissue fusion elements 16, 18 and the generally circular region within the graft mating region 14 is free from subsequent removal. Fluid communication is thus established between the inner lumen of the graft conduit 10 and the blood vessel 12. In an alternate embodiment, fluid communication may be established by manually cutting an aperture within the generally circular union between the graft conduit 10 and the blood vessel 12.

The first and second tissue fusion elements 16,18 are shown by way of example only, disposed within structural elements 20,22. Structural elements 20, 22 are meant to generally denote a vehicle for disposing the tissue fusion elements 16, 18 in position on either side of the graft mating region 14. As will be discussed in detail below, a variety of other such vehicles may be employed to serve this purpose without departing from the scope of the present invention. The process of creating an end-to-side anastomosis (FIG. 2) may be facilitated by optionally employing a mechanism for retaining or biasing the distal end of the graft conduit 10 inwardly about the end of the structural element 20. By way of example only, such a retaining or biasing mechanism may comprise a mesh section 24 disposed along the distal surface of the structural element 20. The mesh section 24 serves this retaining or biasing function by providing a surface through which a physician may secure one or more sutures 26 that extend through the distal end of the graft conduit 10. In this fashion, establishment of the graft mating region 14 is ensured such that, when activated, the first and second tissue fusion elements 16, 18 fuse and thus form a secure end-to-side anastomosis.

Figure 3:
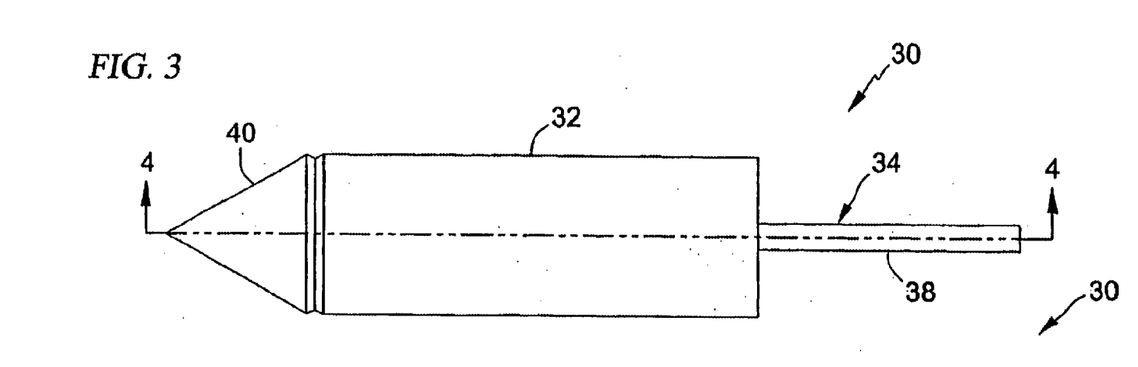
FIG. 3 is a side view illustrating an anastomosis system according to one exemplary embodiment of the present invention particularly suited for creating a side-to-side anastomosis.
Figures 4, 5:
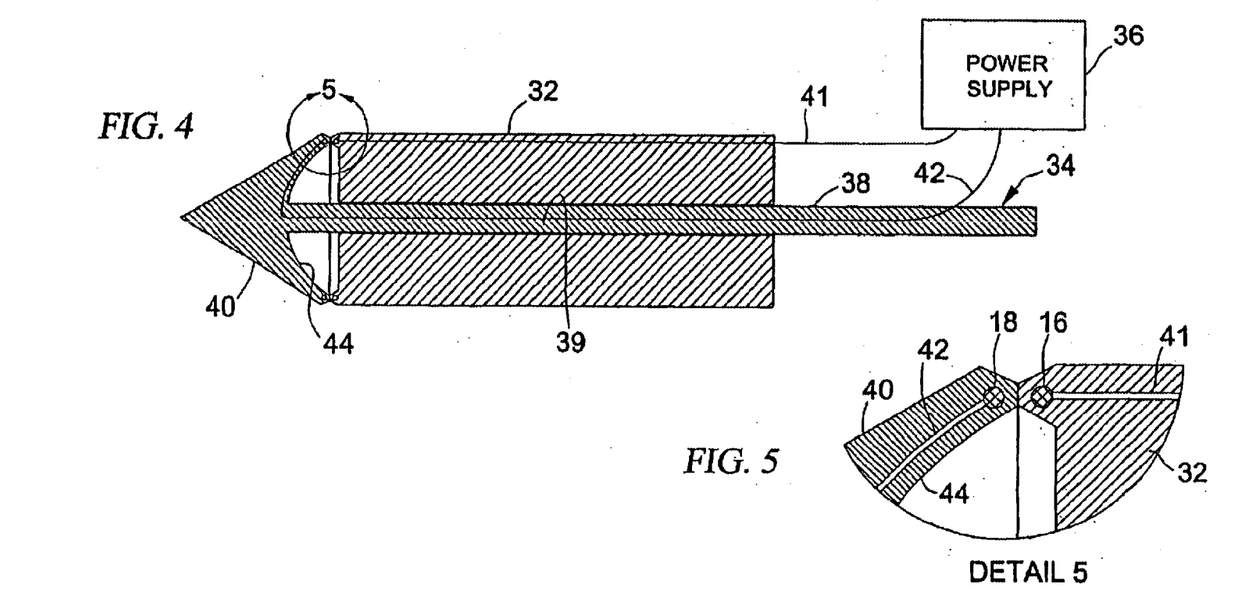
FIG. 4 is a partial-sectional view illustrating the anastomosis system as taken along lines 4—4 of FIG. 3.
FIG. 5 is an enlarged cross-sectional view illustrating the portion of the anastomosis system within detail 5 of FIG. 4.
Figure 6:
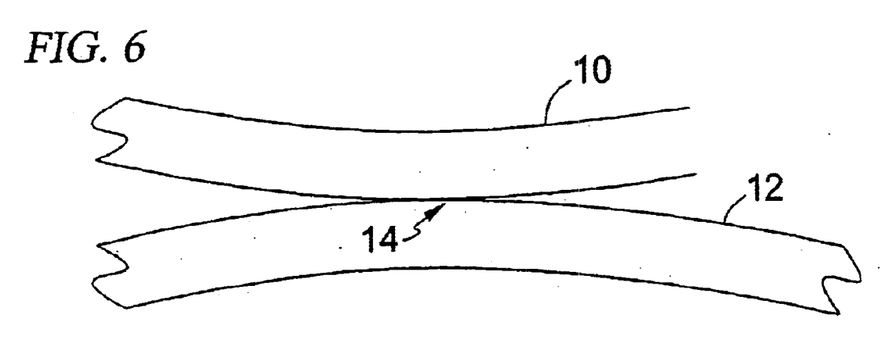
FIGS. 6–11 are side views illustrating the method steps in creating a side-to-side anastomosis according to one embodiment of the present invention, using the anastomosis system shown in FIGS. 3–5.
Figure 7:
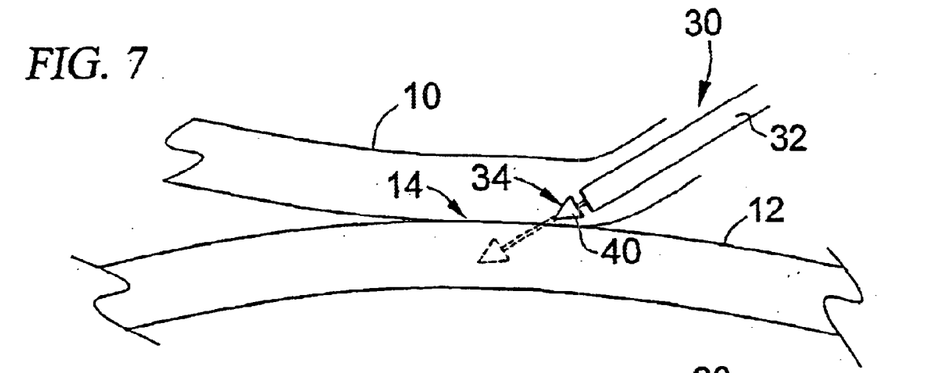
Figure 8:
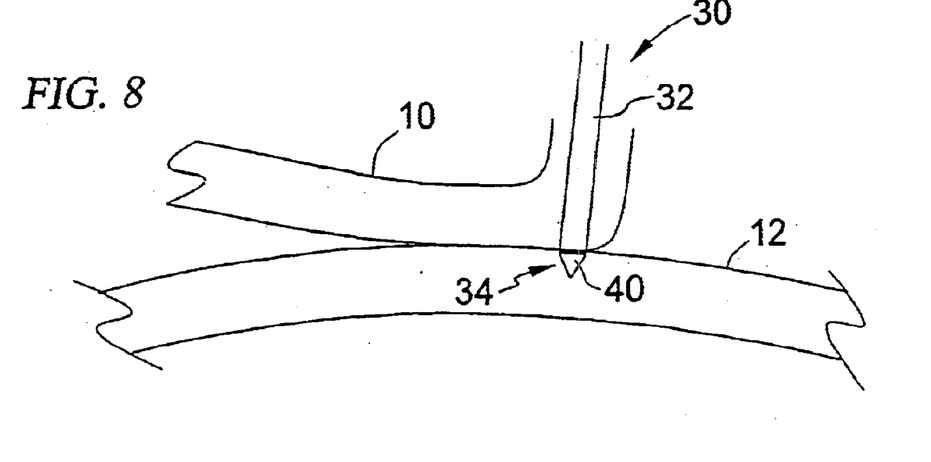
Figure 9:
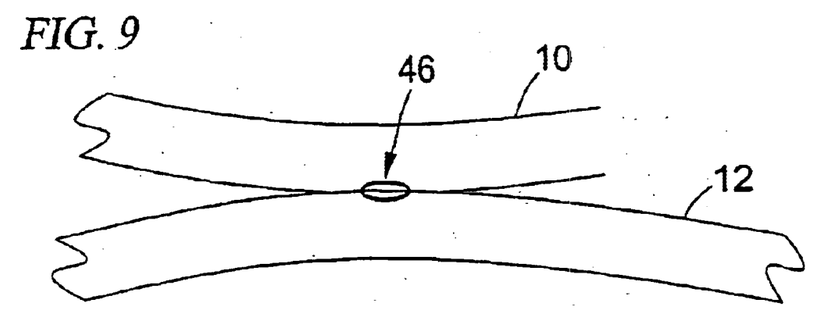
Figure 10:
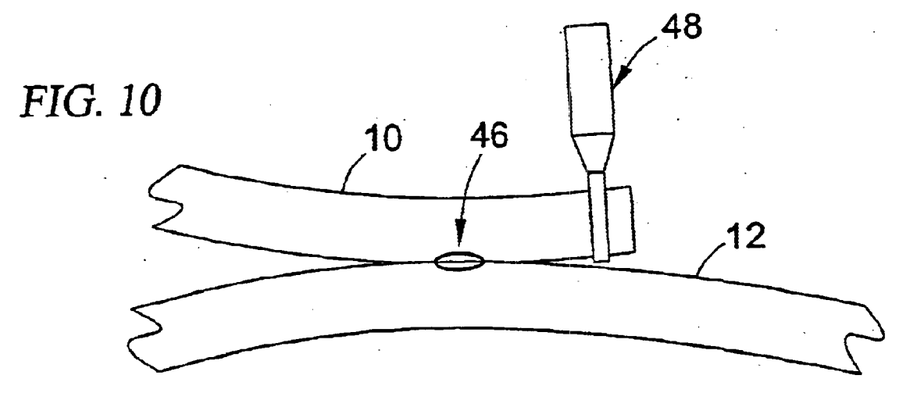
Figure 11:
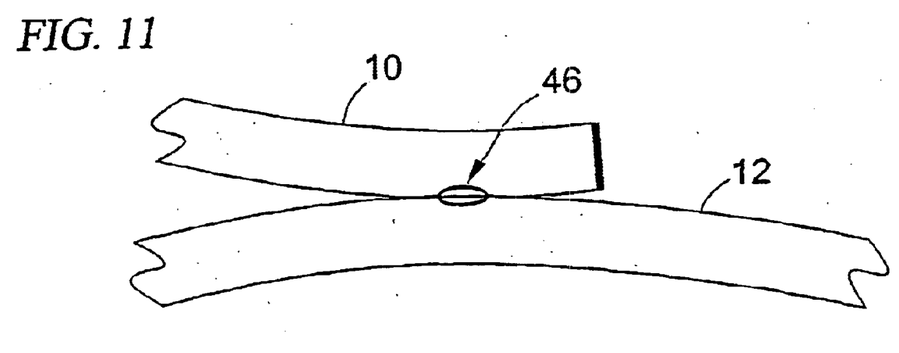

FIGS. 3–5 illustrate an anastomosis system 30 according to one embodiment of the present invention. The anastomosis system 30 comprises a generally cylindrical base member 32 which houses the generally ring-shaped tissue fusion element 16, a penetrating member 34 which houses the generally ring-shaped tissue fusion element 18, and a power supply 36 for activating the first and second tissue fusion elements 16, 18. The base member 32 and the penetrating member 34 provide a mechanism for disposing the first and second tissue fusion elements 16, 18 on either side of a graft mating region 14 as shown in FIGS. 1–2. More specifically, the penetrating member 34 includes an elongated section 38 slideably disposed within a lumen 39 formed in the base member 32 and a tissue-piercing section 40 having the tissue fusion element 18 disposed near its proximal end. In this fashion, the tissue-piercing section 38 may be selectively advanced through the graft conduit and blood vessel (in a side-to-side anastomosis) and then retracted to position the second tissue fusion element 18 against the inside of the blood vessel. The power supply 36 may be coupled to the first and second tissue fusion elements 16, 18 through the use of electrical wire 41,42.

FIGS. 6–11 illustrate a method of creating a side-to-side anastomosis according to a broad aspect of the present invention, employing (by way of example) the anastomosis system 30 shown in FIGS. 3–5. The first step (FIG. 6) involves positioning the graft conduit 10 in a mating relationship with a portion of the blood vessel 12. Doing so creates the graft mating region shown generally at 14. The second step (FIG. 7) involves introducing the base member 32 and penetrating member 34 of the anastomosis system 30 through the open distal end of the graft conduit 10 and advancing the tissue-piercing section 40 through the sidewall of the graft conduit 10 and blood vessel 12 within the graft mating region 14. Although no shown, the travel of the penetrating member 34 may be restricted in any number of fashions such that the tissue-piercing section 40 will be unable to advance far enough to penetrate through the opposite wall of the blood vessel 12. The next step (FIG. 8) involves withdrawing the penetrating member 34 such that the first and second tissue fusion elements 16, 18 are disposed on either side of the graft mating region 14. The power supply may then be activated such that the first and second tissue fusion elements 16, 18 effectively fuse or weld the graft conduit 10 to the blood vessel 12. In a preferred embodiment, the tissue fusion elements 16, 18 simultaneously sever or cut out a region disposed within the fused or welded region. As shown in FIGS. 4 and 5, the severed region may be easily removed from the anastomosis site within a concavity 44 formed within the tissue-piercing section 40. That is, the base member 32 and penetrating member 34 may be removed immediately following fusion (without being slideably separated) while retaining the severed section within the concavity 40. The result of such fusion and removal is a flow port (shown generally at 46 in FIGS. 9–11) establishing fluid communication between the interior of the graft conduit 10 and the interior of the blood vessel 12. The last step (FIG. 10) involves sealing the open distal end of the graft conduit 10, such as through the use of a tissue-welding or tissue-fusing forceps 48 of a type well known in the art. The end result is a side-to-side anastomosis between the graft conduit 10 and the blood vessel 12 which does not leave any foreign articles (such as staples) exposed to blood flow, and which is easy and takes very little time to perform.

Figure 12:
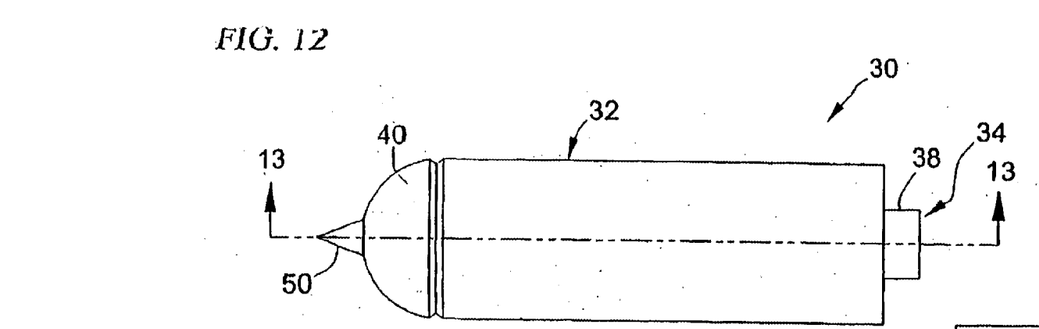
FIG. 12 is a side view illustrating an anastomosis system according to another exemplary embodiment of the present invention.
Figure 13:
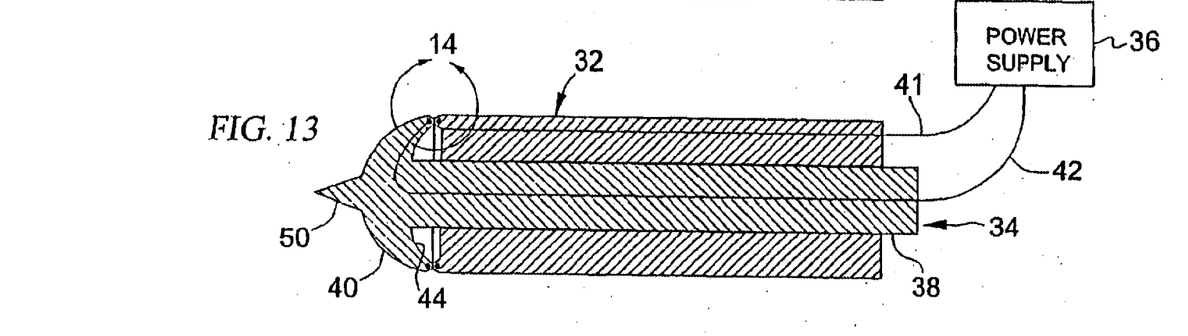
FIG. 13 is a partial-sectional view illustrating the anastomosis system as taken along lines 13—13 of FIG. 12.
Figure 14:
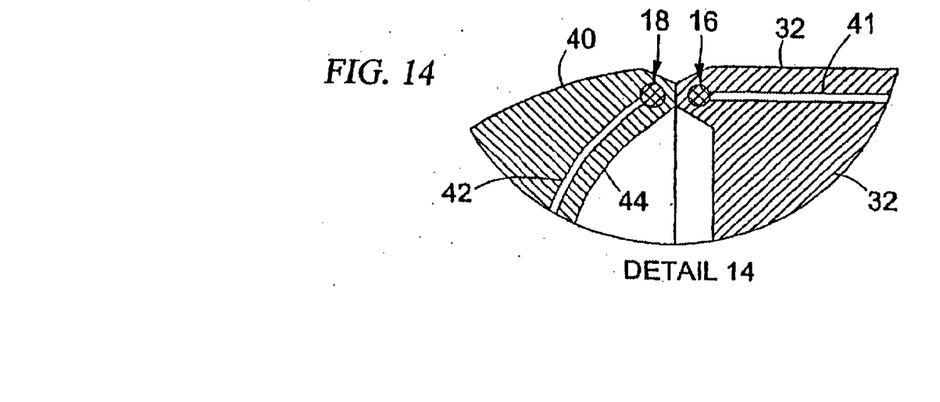
FIG. 14 is an enlarged cross-sectional view illustrating the portion of the anastomosis system within detail 14 of FIG. 13.

The side-to-side anastomosis according to the present invention may be performed using a variety of additional devices embodying the key principles of the present invention. For example, FIGS. 12–14 illustrate an anastomosis system 30 according to another embodiment of the present invention. The anastomosis system 30 is generally similar to the embodiment shown in FIGS. 3–5 with the exception of the penetrating member 34. More specifically, the tissue-piercing section 40 of the penetrating member 34 has a surface of varying pitch between a tip 50 and the remainder of the tissue-piercing section 40. In virtually every other respect, the embodiment of FIGS. 12–14 is identical in design and operation to that previously described with reference to FIGS. 3–5 such that a repeat discussion is not necessary.

Figures 15, 16, 17:
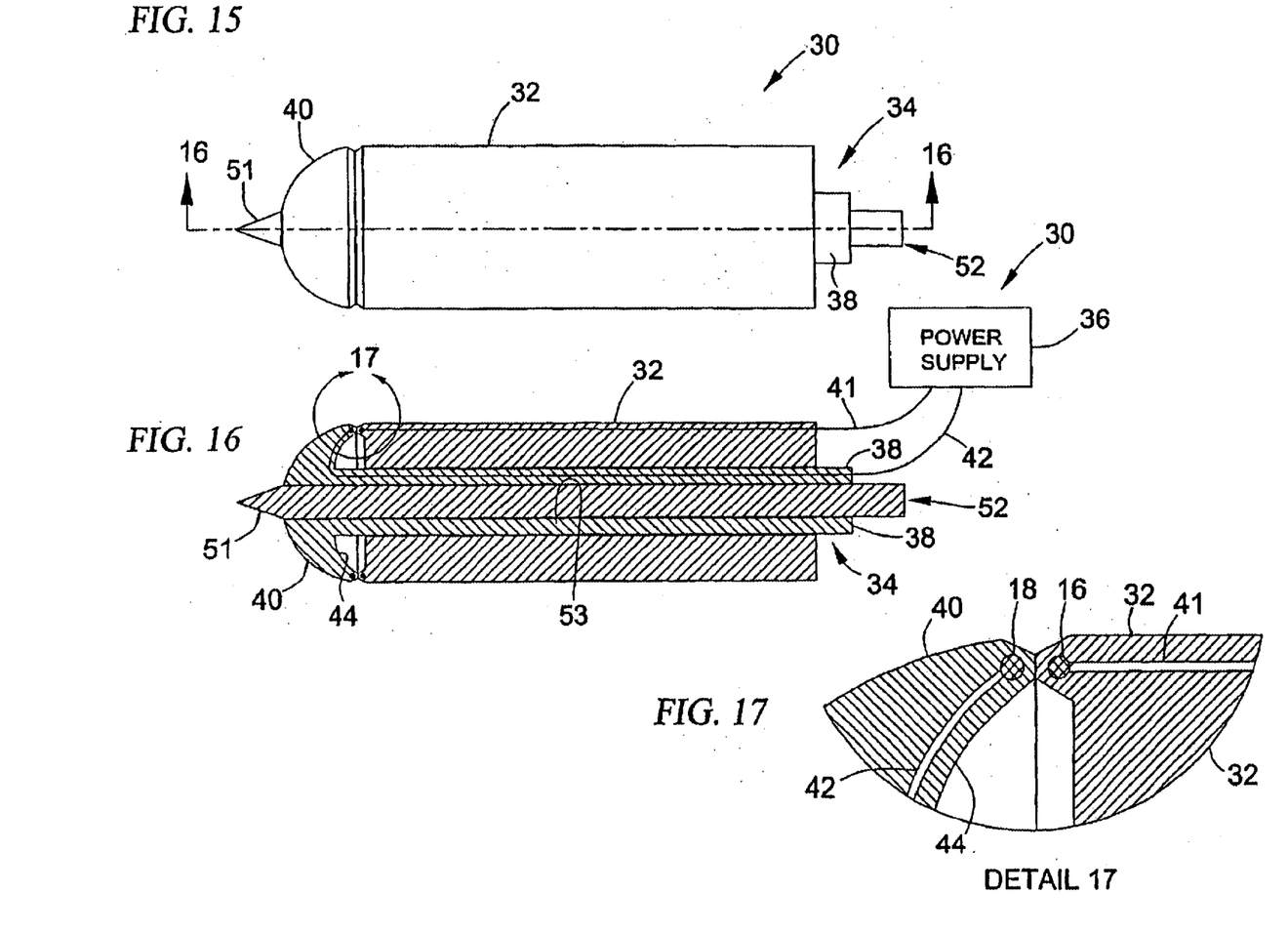
FIG. 15 is a side view illustrating an anastomosis system according to still further exemplary embodiment of the present invention.
FIG. 16 is a partial-sectional view illustrating the anastomosis system as taken along lines 16—16 of FIG. 15.
FIG. 17 is an enlarged cross-sectional view illustrating the portion of the anastomosis system within detail 17 of FIG. 16.

Another system for creating a side-to-side anastomosis according to the present invention is shown in FIGS. 15–17. An anastomosis system 30 is shown according to another embodiment of the present invention. The anastomosis system 30 is generally similar to the embodiment shown above with the exception of the penetrating member 34. More specifically, the penetrating member 34 has an inner lumen 53 for slideably receiving an elongated stylet 52 having a tip 51 which, in use, provides a surface of varying pitch between the tip 50 and the remainder of the tissue-piercing section 40. The sharp tip 51 of the sytlet 52 facilitates piercing through the graft mating region 14 and may be withdrawn (partially or fully) before, during, or after fusion. In virtually every other respect, the embodiment of FIGS. 12–14 is identical in design and operation to that previously described above such that a repeat discussion is not necessary.

Figure 21:
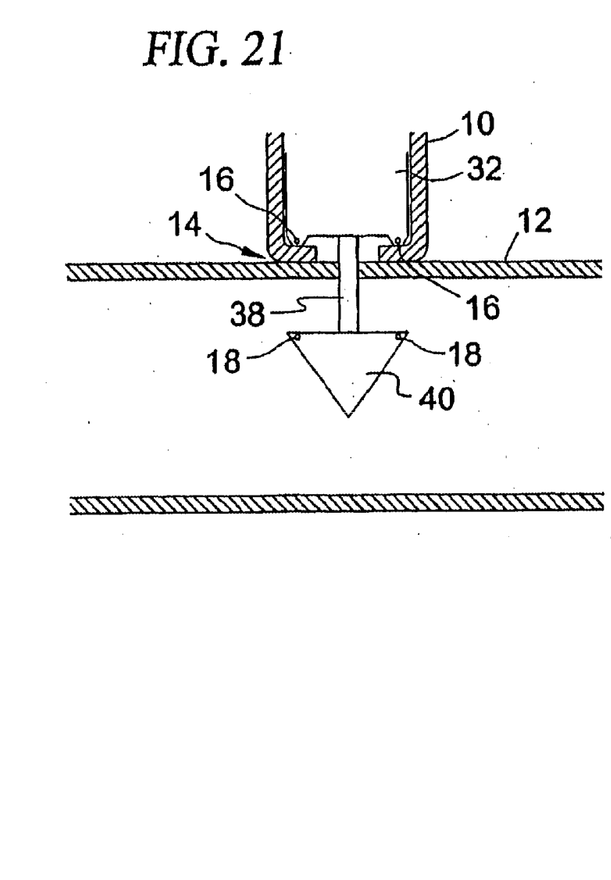
FIGS. 21–23 are side views illustrating the method steps in creating and end-to-side anastomosis according to one embodiment of the present invention.
Figure 22:
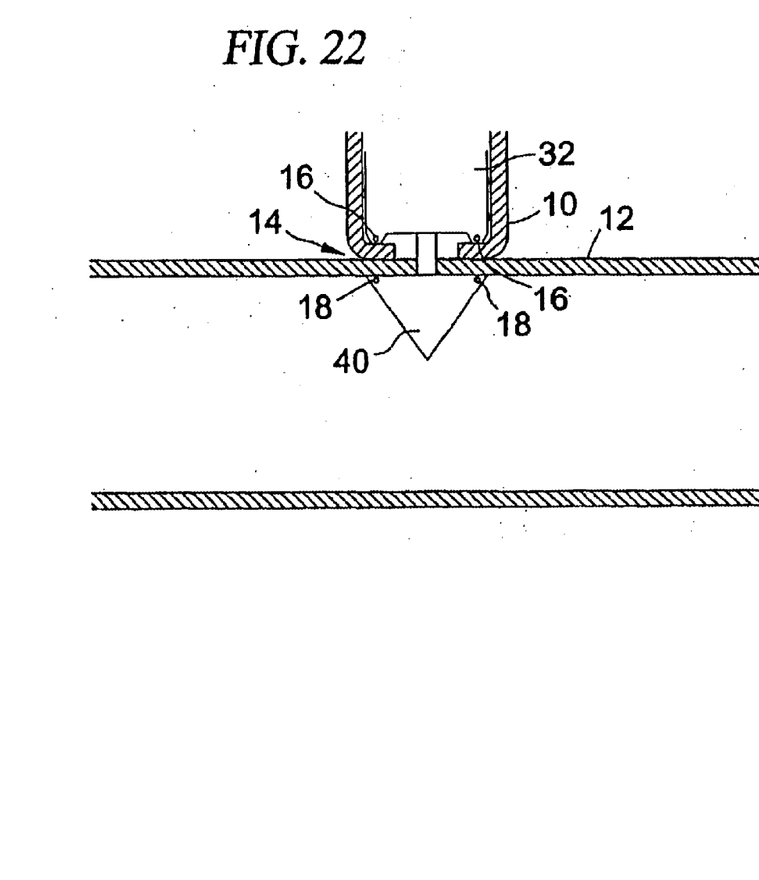

Although the anastomosis system 30 shown in FIGS. 3–5 and 12–17 has been described in terms of forming side-to-side anastomosis according to the present invention, it is to be readily appreciated that these embodiments can be used to perform end-to-side anastomosis as well. For example, the distal end of the graft conduit 10 may be maintained in position over the first tissue fusion element 16 (as shown in FIG. 2) without the use of the mesh section 24. This may be accomplished by simply sandwiching the distal end of the graft conduit 10 in between the proximal end of the tissue-piercing section 40 and the distal end of the base member 32 until the proximal end of the tissue-piercing section 40 is approximately through the wall of the blood vessel 12. At that point, the penetrating member 34 may be advance completely through the blood vessel 12 while maintaining the base member 32 in position with the distal end of the graft conduit 10 sandwiched against the exterior of the blood vessel 12. The first and second tissue fusion elements 16, 18 are then in position such that they may be activated via the power supply 36 to fuse the end of the graft conduit 10 to the side of the blood vessel 12. Once again, in a preferred embodiment, this fusion process will also cut or sever the region disposed within the ring-shaped first and second tissue fusion elements 16, 18. Due to the concavity 44, the cut or severed material may be easily removed by simply maintaining the tissue-piercing section 40 in close proximity to the base member 32 during removal. This process is represented generally in FIGS. 21–23.

Figures 18, 19, 20:
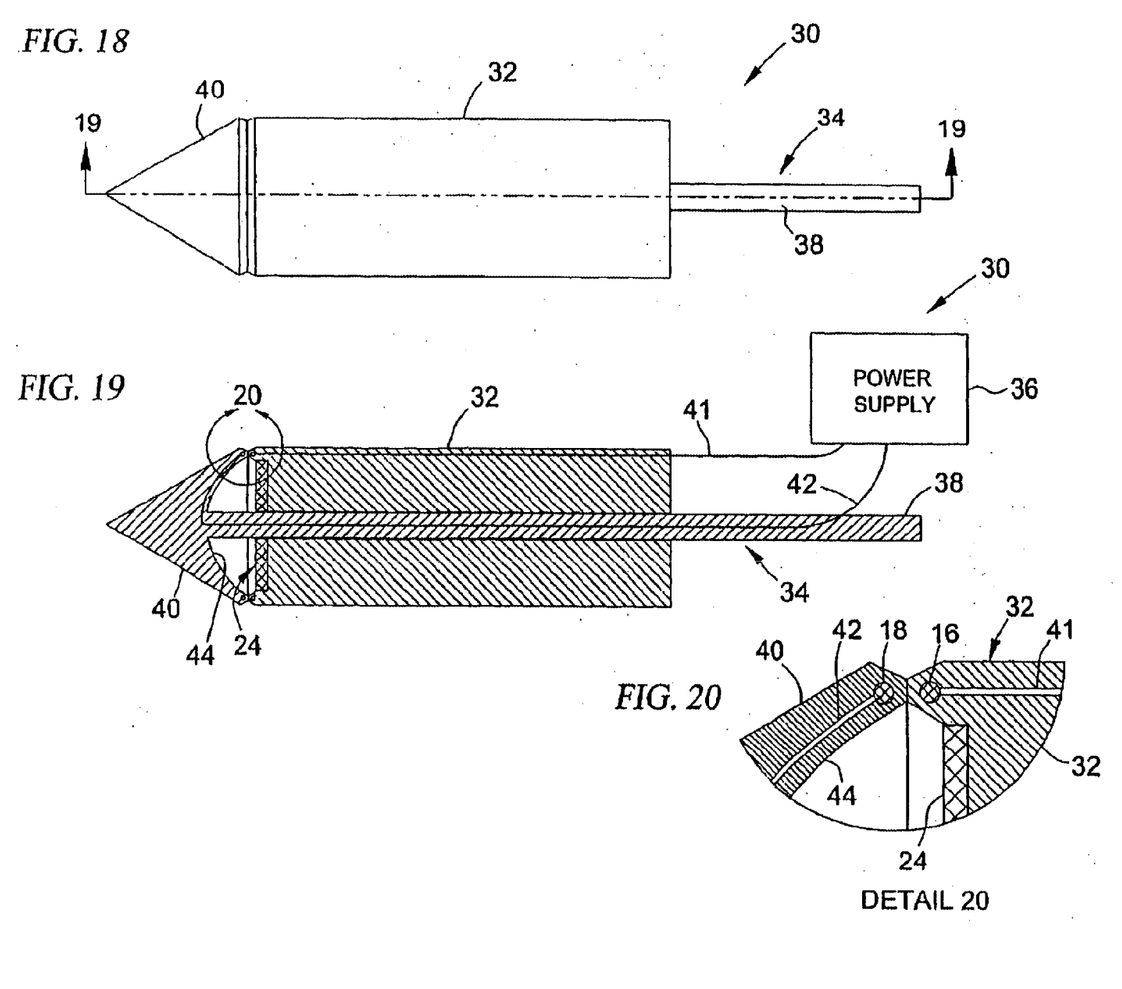
FIG. 18 is a side view illustrating an anastomosis system according to still further exemplary embodiment of the present invention.
FIG. 19 is a partial-sectional view illustrating the anastomosis system as taken along lines 19—19 of FIG. 18.
FIG. 20 is an enlarged cross-sectional view illustrating the portion of the anastomosis system within detail 20 of FIG. 19.
Figure 23:
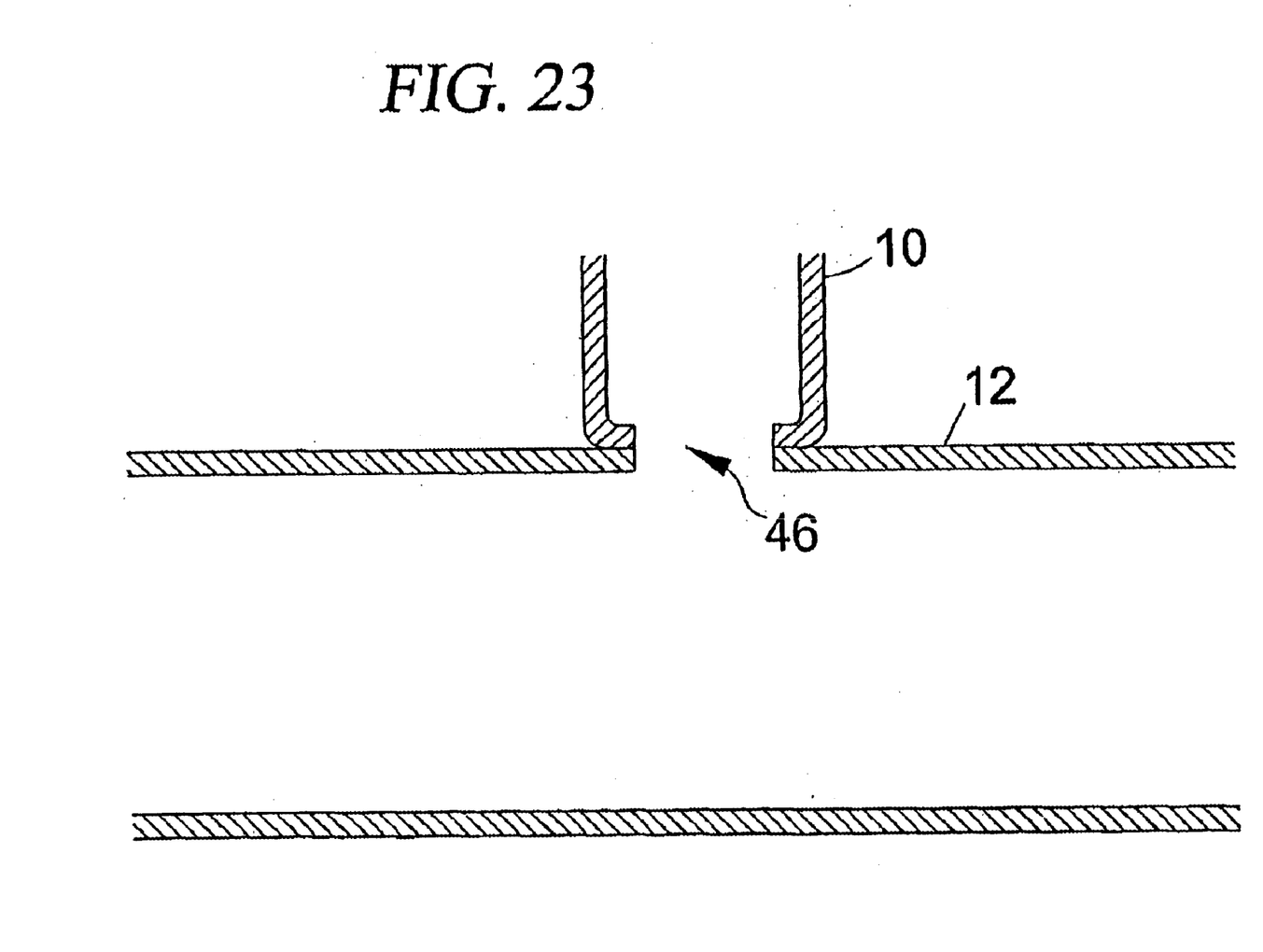

According to yet another embodiment of the present invention, a mechanism or device may be provided to aid in maintaining the distal end of the graft conduit 10 in proper position for an end-to-side anastomosis. For example, as shown in FIGS. 18–20 (and explained briefly above with reference to FIG. 2), the anastomosis system 30 may be equipped with a mesh section 24 along the distal end of the base member 32. The mesh section 24 may allow a surgeon to suture the end of the graft conduit 10 to the end of the base member 32 to maintain it in that position during introduction into the anastomosis site. Following introduction, the tissue-piercing section 40 may be advanced in the manner described above to the position the first and second tissue fusion elements 16, 18 on either side of the graft mating region 14 (FIGS. 21–22), after which point the fusion process may be undertaken to fuse the graft conduit 10 to the blood vessel 12, leaving a flow port 46 therebetween (FIG. 23).

Figure 24:
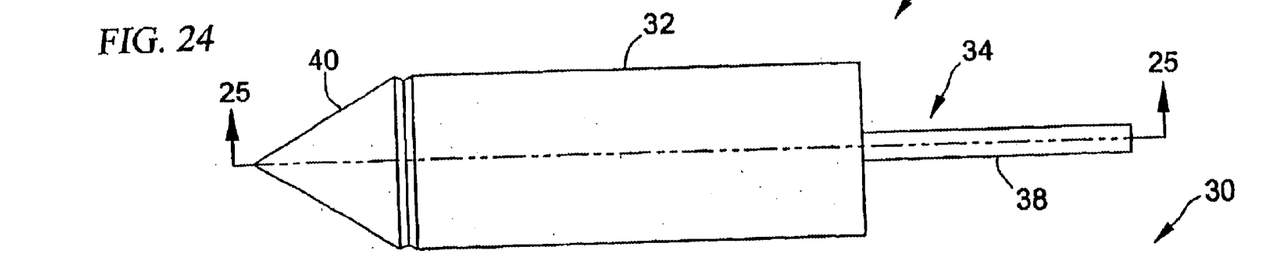
FIG. 24 is a side view illustrating an anastomosis system according to still further exemplary embodiment of the present invention.
Figures 25, 26:
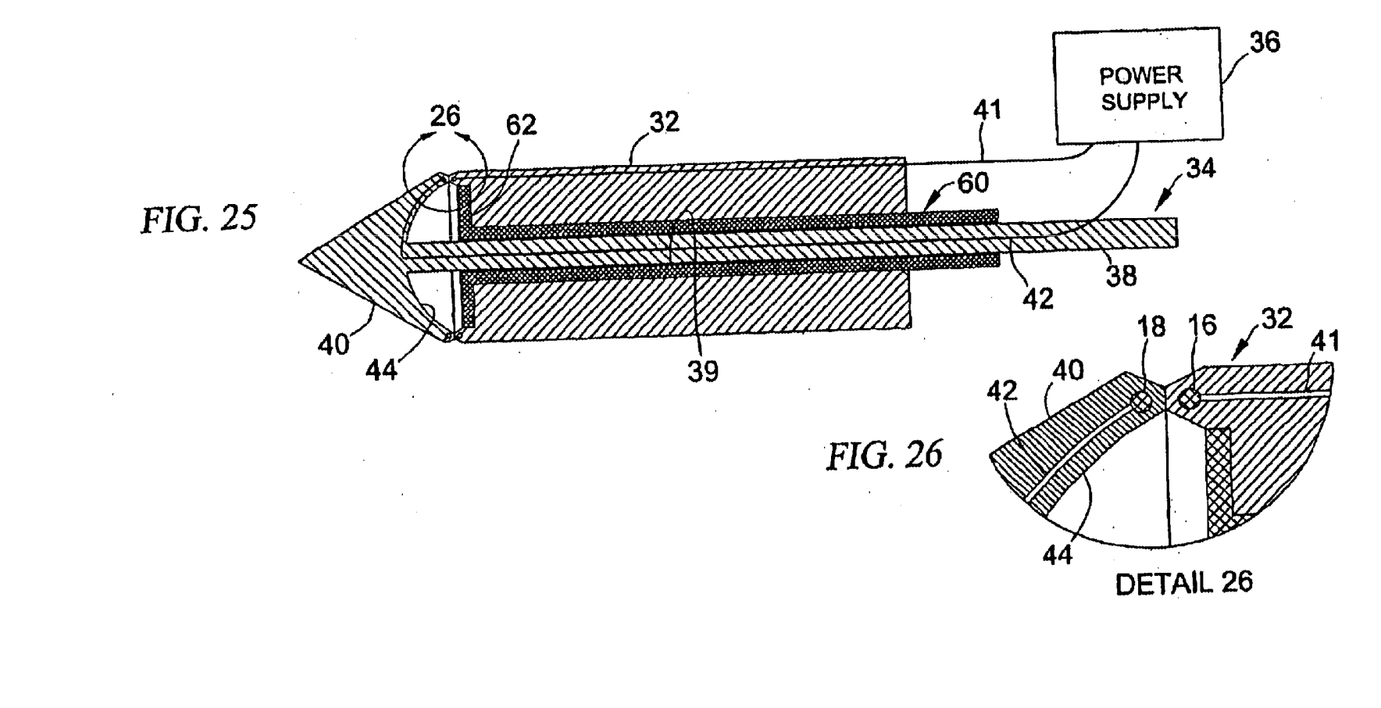
FIG. 25 is a partial-sectional view illustrating the anastomosis system as taken along lines 25—25 of FIG. 24.
FIG. 26 is an enlarged cross-sectional view illustrating the portion of the anastomosis system within detail 26 of FIG. 25.

The end-to-side anastomosis according to the present invention may be performed using a variety of additional devices embodying the key principles of the present invention. For example, FIGS. 24–26 illustrate an anastomosis system 30 according to another embodiment of the present invention. The anastomosis system 30 is generally similar to the embodiment shown in FIGS. 18–20 with the exception of the manner of retaining the distal end of the graft conduit 10 during introduction. More specifically, a slideable retaining member 60 is provided within the lumen 39 within the base member 32. The retaining member 60 includes a flange 62 which, due to the slideable relation of the retaining member 60, may be selectively advanced to receive the distal end of the graft conduit 10 therein and then withdrawn to sandwich the distal end of the graft conduit 10 therein until after the fusion process. In virtually every other respect, this embodiment is identical in design and operation to that previously described with reference to FIGS. 1 and 18–20 such that a repeat discussion is not necessary.

What is claimed is:

1. A device for welding biological tissue comprising a base member having a lumen and a first tissue fusion element, the base member comprising a mesh section configured for securing sutures; and a penetrating member having an elongated section slideably disposed within the lumen and a tissue-piercing section having a second tissue fusion element, the first and second tissue fusion elements adapted to be coupled to a power supply.

2. A device for welding biological tissue comprising a base member having a lumen and a first tissue fusion element, the lumen providing a slideable retaining member including a flange; and a penetrating member having an elongated section slideably disposed within the lumen and a tissue-piercing section having a second tissue fusion element, the first and second tissue fusion elements adapted to be coupled to a power supply.

* * * * *